United States Patent
Hwang et al.

(10) Patent No.: US 9,180,306 B2
(45) Date of Patent: Nov. 10, 2015

(54) PORTABLE MAGNETIC STIMULATION TYPE MEDICALCARE DEVICE

(75) Inventors: Do Guwn Hwang, Wonju-si (KR); Syung Hyun Cho, Seoul (KR); Byung Jae Kim, Wonju-si (KR); Sang Dae Choi, Wonju-si (KR)

(73) Assignee: SANGJI UNIVERSITY INDUSTRY ACADEMIC COOPERATION FOUNDATION, Wonju-si (KR)

( * ) Notice: Subject to any disclaimer, the term of this patent is extended or adjusted under 35 U.S.C. 154(b) by 758 days.

(21) Appl. No.: 13/388,162

(22) PCT Filed: Jul. 29, 2010

(86) PCT No.: PCT/KR2010/004980
§ 371 (c)(1),
(2), (4) Date: Apr. 16, 2012

(87) PCT Pub. No.: WO2011/014017
PCT Pub. Date: Feb. 3, 2011

(65) Prior Publication Data
US 2012/0197064 A1 Aug. 2, 2012

(30) Foreign Application Priority Data
Jul. 31, 2009 (KR) ........................ 10-2009-0070944

(51) Int. Cl.
*A61N 2/02* (2006.01)
*A61N 1/32* (2006.01)
*A61N 1/40* (2006.01)
*A61N 2/00* (2006.01)

(52) U.S. Cl.
CPC . *A61N 2/02* (2013.01); *A61N 1/321* (2013.01); *A61N 1/40* (2013.01); *A61N 2/004* (2013.01)

(58) Field of Classification Search
CPC .......... A61N 2/02; A61N 1/40; A61N 2/006; A61N 2/008; A61N 1/0484; A61N 1/36021; A61N 1/36071; A61N 2/12; A61N 2/00; A61N 1/32
USPC ....................................................... 600/9–15
See application file for complete search history.

(56) References Cited

U.S. PATENT DOCUMENTS 4,989,604 A * 2/1991 Fang ................................. 607/2
2003/0158585 A1 * 8/2003 Burnett ........................... 607/2

FOREIGN PATENT DOCUMENTS

| JP | 2000-254239 | 9/2000 | |
| KR | 10-0816254 | 3/2008 | |
| KR | 10-2008-0061463 | 7/2008 | |
| KR | 10-2008-0061465 | 7/2008 | |
| WO | WO 2006057532 A1 * | 6/2006 | .............. H02M 3/28 |

OTHER PUBLICATIONS

International Search Report for PCT/KR2010/004980, mailed Apr. 22, 2011.

* cited by examiner

Primary Examiner — Christine H Matthews
(74) Attorney, Agent, or Firm — Nixon & Vanderhye P.C.

(57) ABSTRACT

Provided is a magnetic stimulation type medical care device including a main body for generating a magnetic stimulation and various probes electrically connected to the main body to stimulate a skin of a patient through non-contact deep penetration. The magnetic stimulation type medical care device includes a main body for generating a voltage and at least one probe in which a coil for generating a magnetic field from the voltage generated in the main body is built, the at least one probe being electrically connected to the main body.

10 Claims, 15 Drawing Sheets

PORTABLE MAGNETIC STIMULATION TYPE MEDICALCARE DEVICE

This application is the U.S. national phase of International Application No. PCT/KR2010/004980, filed 29 Jul. 2010, which designated the U.S. and claims priority to KR Application No. 10-2009-0070944, filed 31 Jul. 2009, the entire contents of each of which are hereby incorporated by reference.

TECHNICAL FIELD

The present invention relates to a magnetic curer using a voltage generation apparatus, and more particularly, to a portable magnetic stimulation type medicalcare device in which a probe may be adequately replaced for each portion of a human body.

BACKGROUND ART

In general, stimulation methods for curing a neuromuscular system of a human body may be classified into an electrical stimulation method and a magnetic stimulation method.

Among these, the magnetic stimulation method is a method in which magnetic energy obtained by discharging a voltage charged in a condenser into a magnetic field generation coil is induced into skins or tissues of the human body to generate an eddy current, thereby stimulating the neuromuscular system.

A generation principle of the magnetic stimulation is based on the Faraday's law of electromagnetic induction. In the Faraday's law of electromagnetic induction, a magnetic flux linked with a circuit is changed, an electromotive force (EMF), which is be in proportion to a rate at which a magnetic flux is reduced, is induced in the circuit. Here, the induced current flowing into the circuit by the electromagnetic induction flows in a direction opposite to that of the magnetic flux linked with the circuit.

The magnetic stimulation has a characteristic in which non-contact deep penetration is possible. That is, the magnetic stimulation has advantages in that the magnetic stimulation has a superior penetration effect when compared to that of the electrical stimulation and does not have pains or unpleasant feeling due to the electrical stimulation. Thus, the magnetic stimulation is being in the spotlight for a use of curer.

However, magnetic curers developed so far are developed as products for hospitals and thus are expensive. Also, since the magnetic curers are limited in use, the magnetic curers are not adequate for a structure that can be used for each portion of a human body in home.

DISCLOSURE

Technical Problem

It is an object of the present invention to provide a portable magnetic stimulation type medicalcare device which is simplified in structure and miniaturized so that the device is used for homes or individuals as well as hospitals and is easily portable and inexpensive, and also adequately and selectively utilizes probes having specific shapes according to portions of the human body.

Technical Solution

In accordance with an exemplary embodiment, a magnetic stimulation type medicalcare device includes: a main body for generating a voltage; and at least one probe in which a coil for generating a magnetic field from the voltage generated in the main body is built, the at least one probe being electrically connected to the main body. The main body may include: an alternating current (AC) voltage supply part; a transformer connected to the AC voltage supply part to boost an AC voltage; a voltage supply regulation part for regulating the AC voltage flowing from the AC voltage supply part into the transformer; a diode for rectifying and charging the AC voltage boosted by the transformer; and a control part for discharging the voltage into a coil within the probe and controlling the AC voltage regulation by the AC supply regulation part. The probe may include: a stick-type probe grasped by a hand and used for each portion of a human body; a joint-type probe worn on a portion of a joint such as a knee; and a pelvis-type probe seated on buttocks, wherein the probes are selectively connected to the main body.

Advantageous Effects

As described above, the magnetic stimulation type medicalcare device may be miniaturized to be used for individuals. Also, the magnetic stimulation type medicalcare device may be portable and inexpensive. Since each of the probes may be detachably coupled to the main body, the probes may be easily replaced with each other according to the portions of the human body of the patient to be cured.

MODE FOR INVENTION

Hereinafter, preferred embodiments of the present invention will be described in detail with reference to the accompanying drawings.

Figure 1:
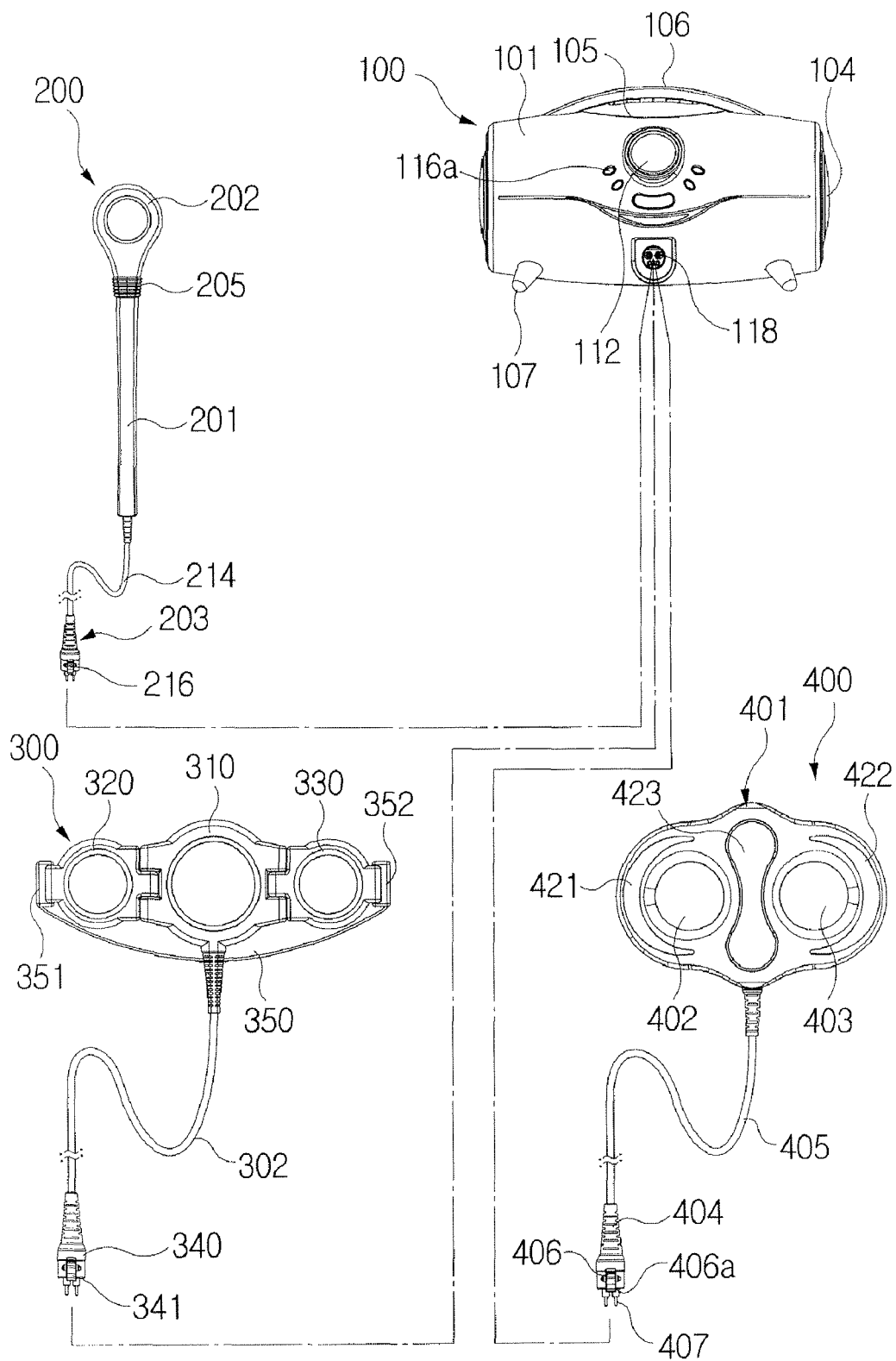
FIG. 1 is a view illustrating the whole structure of a magnetic stimulation type medicalcare device according to the present invention.

Referring to FIG. 1, a magnetic stimulation type medicalcare device according to the present invention includes a main body 100 that is a voltage generation apparatus and a plurality of probes 200, 300, and 400 connected to a side of the main body 100 and respectively including coils for generating a magnetic field from a voltage generated in the main body 100.

Each of the probes 200, 300, and 400 may be selectively connected to the main body 100. In the current embodiment, the probes 200, 300, and 400 include a stick-type probe 200 grasped by a hand and used for each portion of a human body, a joint-type probe 300 worn on a portion of a joint such as a knee, and a pelvis-type probe 400 seated on buttocks.

Figure 2:
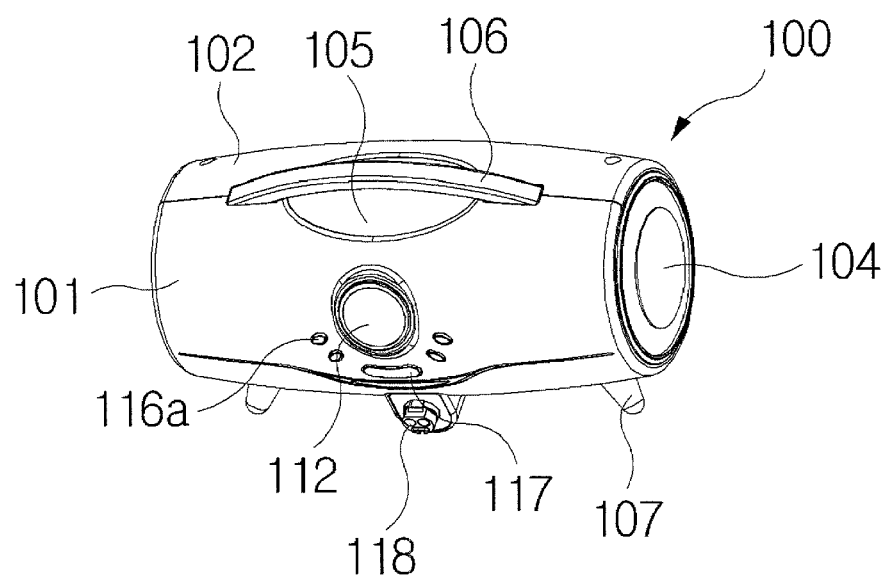
FIG. 2 is a front perspective view illustrating a main body of the magnetic stimulation type medicalcare device according to the present invention.
Figure 3:
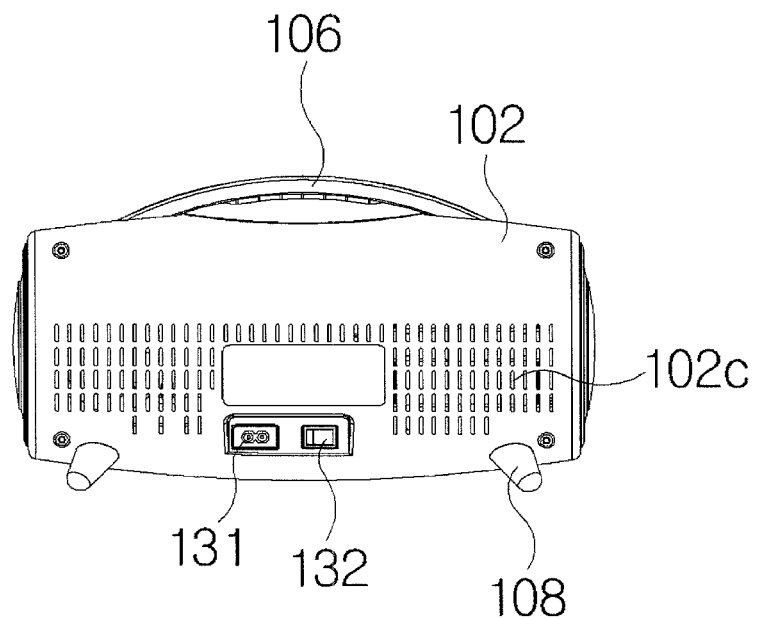
FIG. 3 is a rear surface illustrating the main body of the magnetic stimulation type medicalcare device of FIG. 2.
Figure 4:
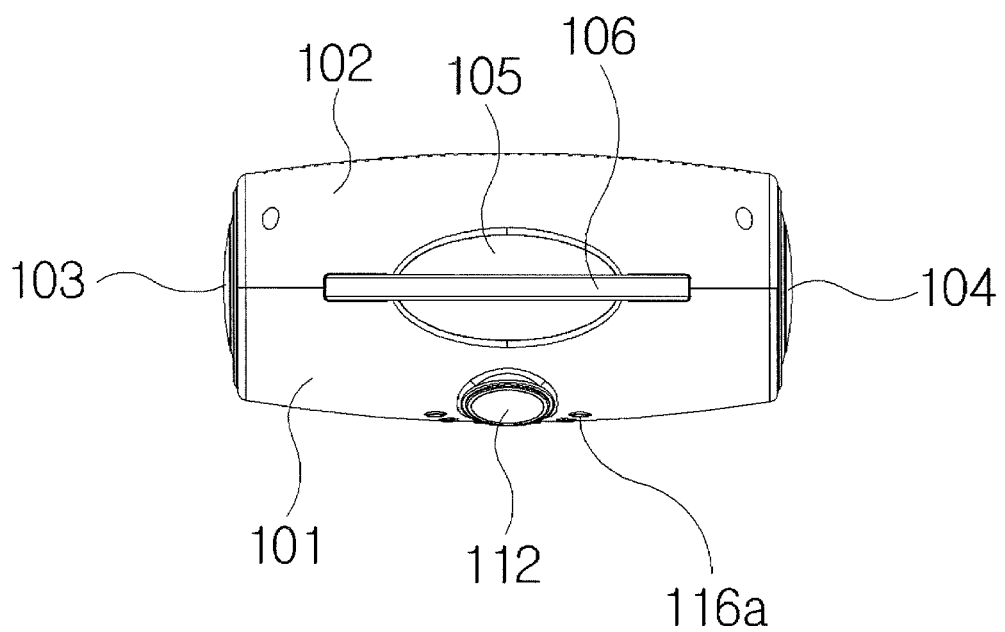
FIG. 4 is a plan view of the main body of the magnetic stimulation type medicalcare device of FIG. 2.
Figure 5:
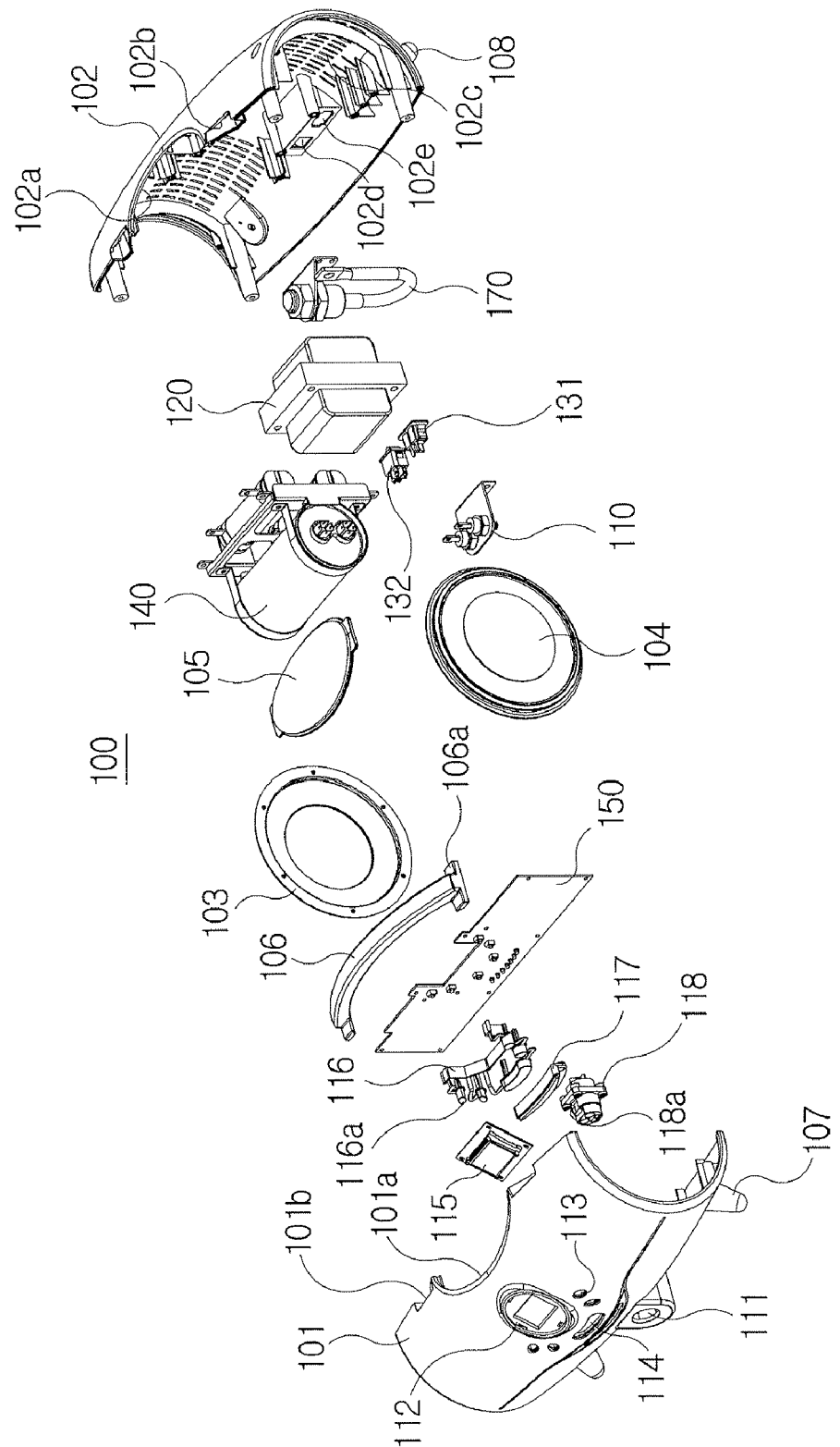
FIG. 5 is an exploded perspective view of the main body of the magnetic stimulation type medicalcare device of FIG. 2.
Figure 6:
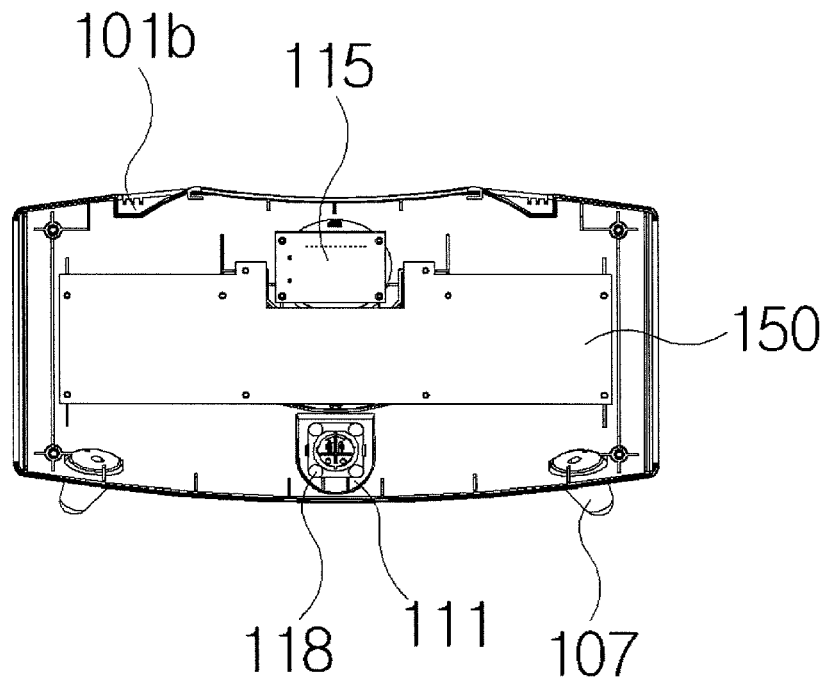
FIG. 6 is a front view illustrating an internal assembly state of the main body of the magnetic stimulation type medicalcare device of FIG. 2.
Figure 7:
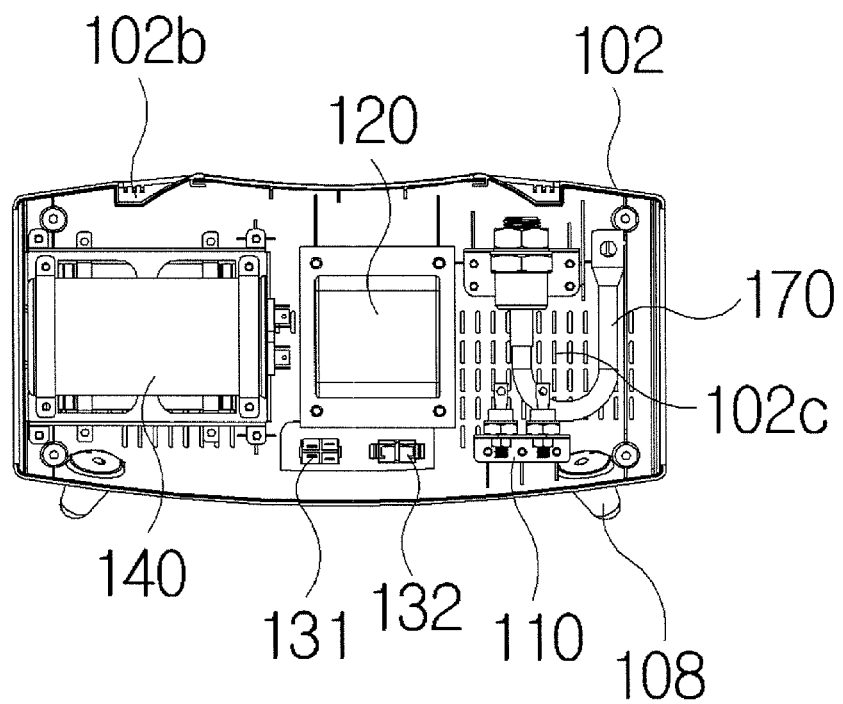
FIG. 7 is a rear view illustrating the internal assembly state of the main body of the magnetic stimulation type medicalcare device of FIG. 2.

FIG. 2 is a front perspective view illustrating a body of the magnetic stimulation type medicalcare device according to the present invention. FIG. 3 is a rear surface illustrating the body of the magnetic stimulation type medicalcare device of FIG. 2. FIG. 4 is a plan view of the body of the magnetic stimulation type medicalcare device of FIG. 2. FIG. 5 is an exploded perspective view of the body of the magnetic stimulation type medicalcare device of FIG. 2. FIG. 6 is a front view illustrating an internal assembly state of the body of the magnetic stimulation type medicalcare device of FIG. 2. FIG. 7 is a rear view illustrating the internal assembly state of the body of the magnetic stimulation type medicalcare device of FIG. 2.

Referring to FIGS. 2 to 4, the main body 100 of the magnetic stimulation type medicalcare device of the present invention includes a handle 106 for being easily portable and has a convex outer appearance having a cylindrical shape (alternatively, the main body 100 may have outer appearances different from the convex outer appearance) for esthetic feeling.

The main body 100 of the magnetic stimulation type medicalcare device includes front and rear covers 101 and 102 each having a convex curved shape at a middle portion thereof and left and right covers 103 and 104 for respectively covering left and right opened sides. Here, the front and rear covers 101 and 102 and the left and right covers 103 and 104 may be assembled or dissembled with/from each other. Also, a plurality of support legs 107 and 108 corresponding to each other may protrude from lower ends of the front and rear covers 101 and 102 so that the front and rear covers 101 and 102 stand upright by itself.

Referring to FIGS. 5 to 7, the main body 100 of the magnetic stimulation type medicalcare device includes an alternating current (AC) voltage supply part 131, a transformer 120 connected to the AC voltage supply part 131 to boost an AC voltage supplied from the AC voltage supply part 130, a voltage supply regulation part 132 for regulating the AC voltage flowing from the AC voltage supply part 131 into the transformer 120, a diode 140 and capacitor 110 connected to the transformer 120 to rectify and charge the AC voltage boosted by the transformer 120, and a control part 150 for discharging a charge voltage charged in the diode 140 and capacitor 110 into the coils (an internal coil of each probe) and controlling the AC voltage regulation by the AC supply regulation part 132.

Also, in the components constituting the main body 100 of the magnetic stimulation type medicalcare device, the AC voltage supply part 131, the voltage supply regulation part 132, the transformer 120, the diode 140, and the capacitor 110 are disposed at a rear side of the control part 150, and an LCD module 115 that is a display unit, a button assembly 116 on which a plurality of manipulation buttons are assembled, an LED lamp 117, and a connection terminal 118 for connecting the probes to each other are disposed at a front side of the control part 150.

The control part 150 may control an overall operation of the magnetic stimulation type medicalcare device with respect to operations of the components due to the manipulation buttons.

Referring to FIG. 5, the front cover 101 of the main body 100 includes a display part 112 in which the LCD module 115 is mounted inward therefrom, a button hole 113 through which each of the manipulation buttons of the button assembly 116 is drawn out, a lamp part 114 on which the LED lamp 117 is mounted, and a connector part 111 on which the connection terminal 118 is mounted. A vent hole 102c for discharging internal heat to the outside is defined in a surface of the rear cover 101.

In drawings, a non-explained reference numeral "118a" denotes a hook. The hook 118a may be disposed on an upper end of the connection terminal 118 to fix a connection plug of each of the probes that will be described with reference to FIGS. 8 to 22.

The main body 100 of the magnetic stimulation type medicalcare device according to the present invention includes the upper cover 105 having a circular shape on an upper middle portion. The front cover 101 and the rear cover 102 include uneven parts 101a and 102a having semicircular shapes on upper middle portions, respectively. The front cover 101 and the rear cover 102 are coupled to each other so that the upper cover 105 is fixed in a hooked state. The upper cover 105 may have a concave shape so that a user easily grasps the handle 106 disposed on the upper portion thereof. Also, hook protrusions 106a connected to an upper portion of the main body 100 protrude from both ends of the handle 106 in left and right directions. Hook grooves 101b and 102b to which the hook protrusions 106a are coupled to the front and rear covers 101 and 102 and then fixed in the hooked state are defined outside the semicircular-shaped uneven parts 101a and 102a of the front and rear covers 101 and 102, respectively.

Figure 8:
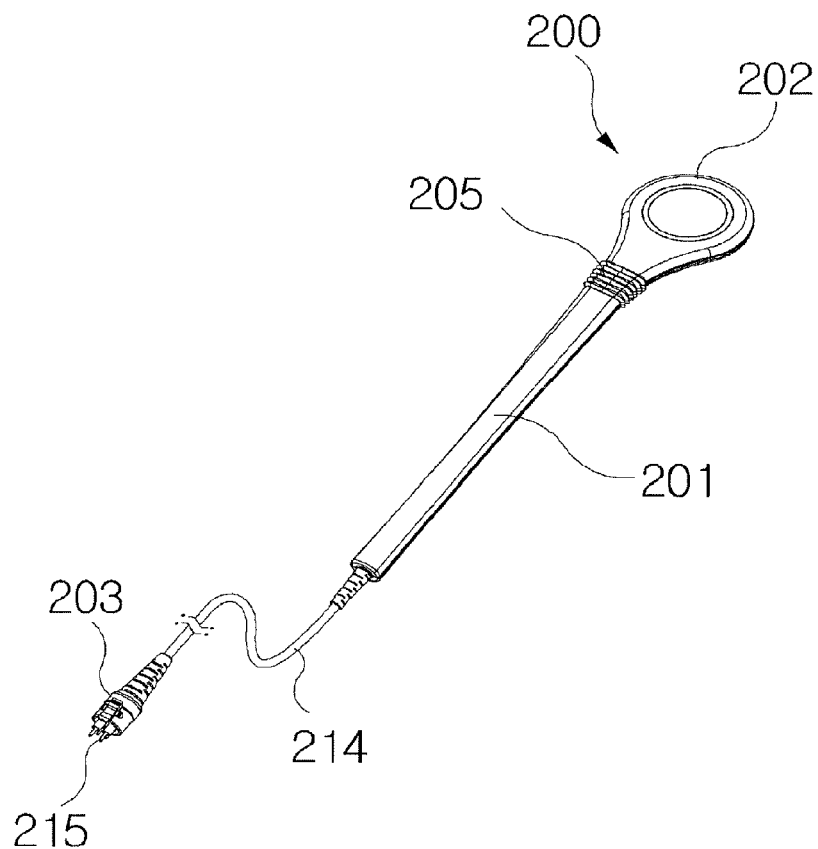
FIG. 8 is a plan perspective view illustrating a stick-type probe of the magnetic stimulation type medicalcare device according to the present invention.
Figure 9:
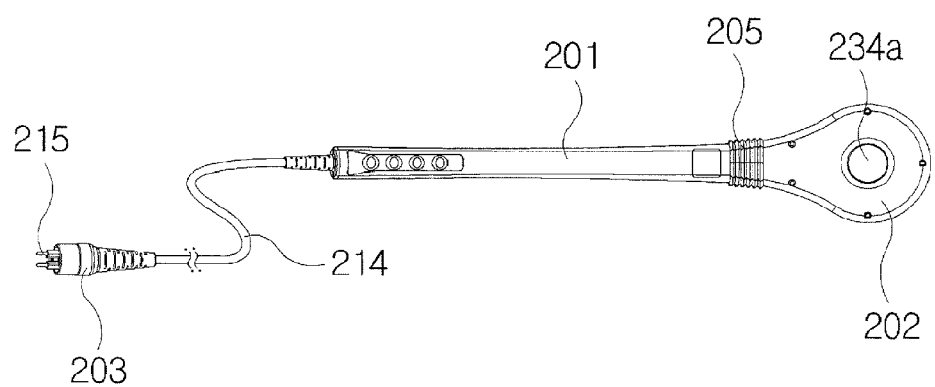
FIG. 9 is a bottom view illustrating the stick-type probe of FIG. 8.
Figure 10:
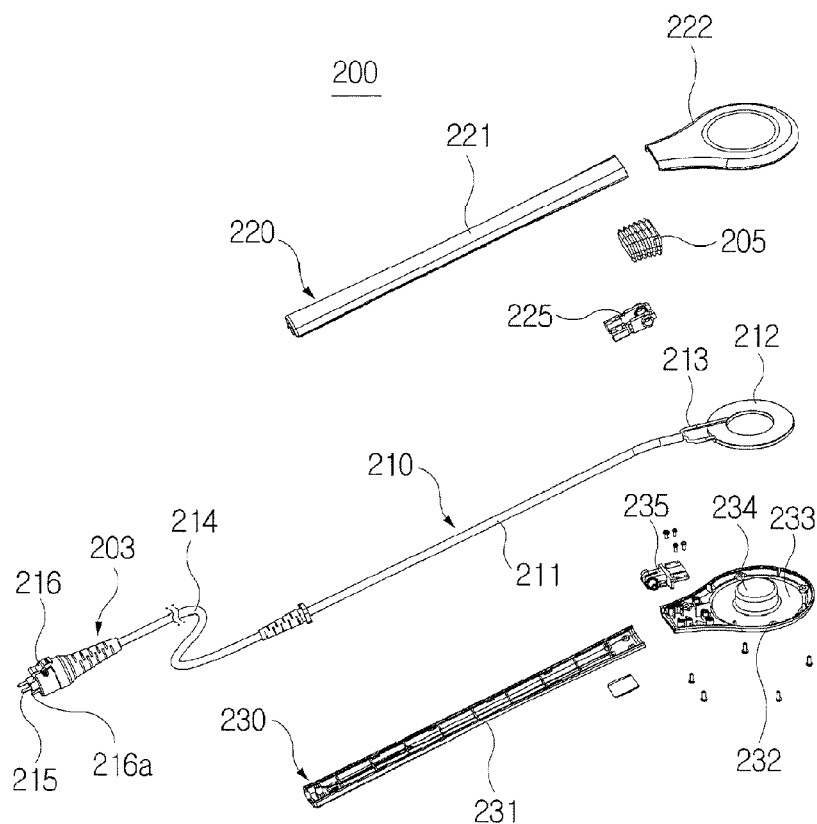
FIG. 10 is an exploded perspective view illustrating the stick-type probe of FIG. 8.
Figure 11:
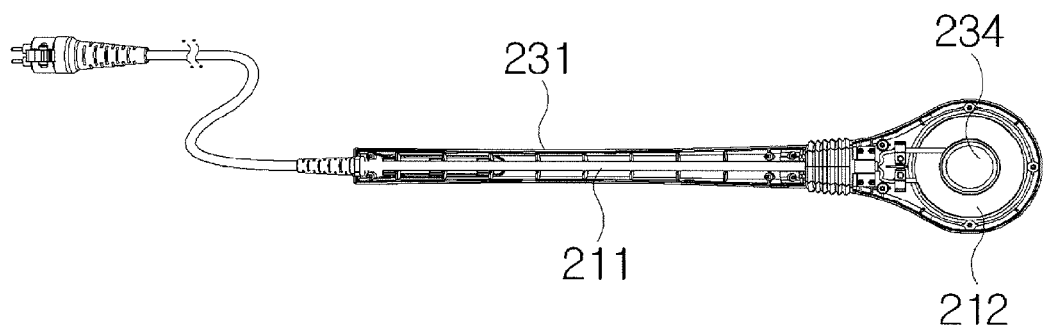
FIG. 11 is a plan view illustrating an internal assembly state of the stick-type probe of FIG. 8.
Figure 12:
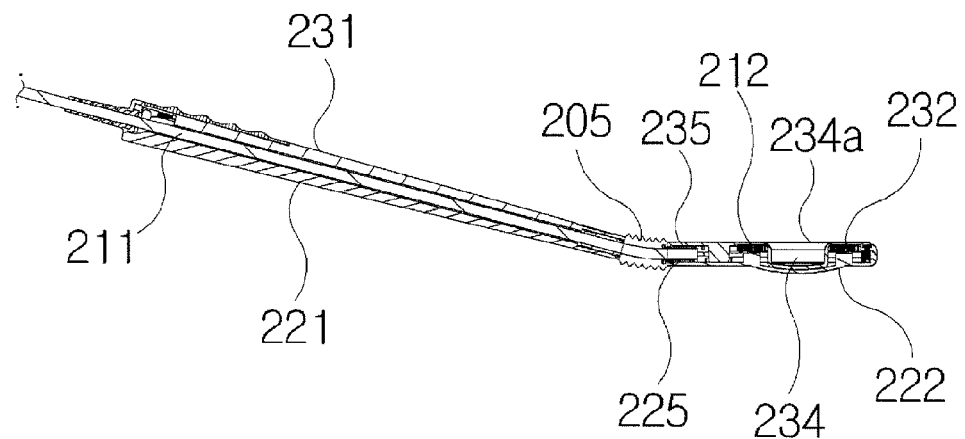
FIG. 12 is a sectional view illustrating a coupled state of the stick-type probe of FIG. 8.

FIG. 8 is a plan perspective view illustrating a stick-type probe of a magnetic stimulation type medicalcare device according to the present invention. FIG. 9 is a bottom view illustrating the stick-type probe of FIG. 8. FIG. 10 is an exploded perspective view illustrating the stick-type probe of FIG. 8. FIG. 11 is a plan view illustrating an internal assembly state of the stick-type probe of FIG. 8. FIG. 12 is a sectional view illustrating a coupled state of the stick-type probe of FIG. 8.

The stick-type probe 200 may be used for various portions of the human body in a state where the user grasps the stick-type probe 200. As shown in FIG. 1, the stick-type probe 200 may be used by connecting a connection plug 203 to the connection terminal 118 of the main body 100 of the magnetic stimulation type medicalcare device. The connection plug 203 includes a coupling member 216 rotatably hinged in a state where a hook protrusion 216a is provided. Also, in a state where the connection plug 203 is connected to the connection terminal 118, the connection plug 203 may be stably connected in a state where the hook protrusion 216a is hooked with the hook (see reference numeral 118a of FIG. 2) of the connection terminal 118.

The stick-type probe 200 includes a coil part 212, into which the discharged voltage is supplied from the main body 100, on an end of a wire part 210 that is an extending part of lead wires 211, 213, and 214. In the current embodiment, the coil part 212 may have a hollow circular plate. The wire part 210 and the coil part 212 may be received into in upper and lower case members 230 for covering the wire part 210 and the coil part 212.

The upper case member 220 and the lower case member 230 include body cases 221 and 231 for covering the wire part 210 and head cases 222 and 232 for covering a portion of the wire part 210 and the coil part 212, respectively. Since the upper and lower case members 220 and 230 are coupled to each other, the stick-type probe 200 may be classified into a stick part 201 in which the wire part 210 is built, a head part 202 in which the coil part 212 is built, and the connection plug 203.

Referring to the coupling structure of the head part 202 in FIGS. 10 to 12, the head case 232 of the lower case member 230 includes a fitting protrusion 234 at a center of a receiving convex part 233 on which the coil part 212 is seated. Thus, the coil part 211 is fixed by the coupling of the head part 202 in a state where the coil part 212 having the hollow plate shape is fitted into the fitting protrusion 234.

Also, in the stick-type probe 200 of the present invention, the heat part 202 may be slightly rotatable. For this, the upper and lower case members 220 and 230 may be connected through hinge members 225 and 235 between the body cases 221 and 231 and the head cases 222 and 232. Here, the hinge members 225 and 235 are covered by a cover member 205 formed of a soft material. As described above, in the stick-type probe 200, the head part 202 may be rotatable with respect to centers of the hinge members 225 and 235 according to an angle of a portion of the human body to be cured.

Figure 13:
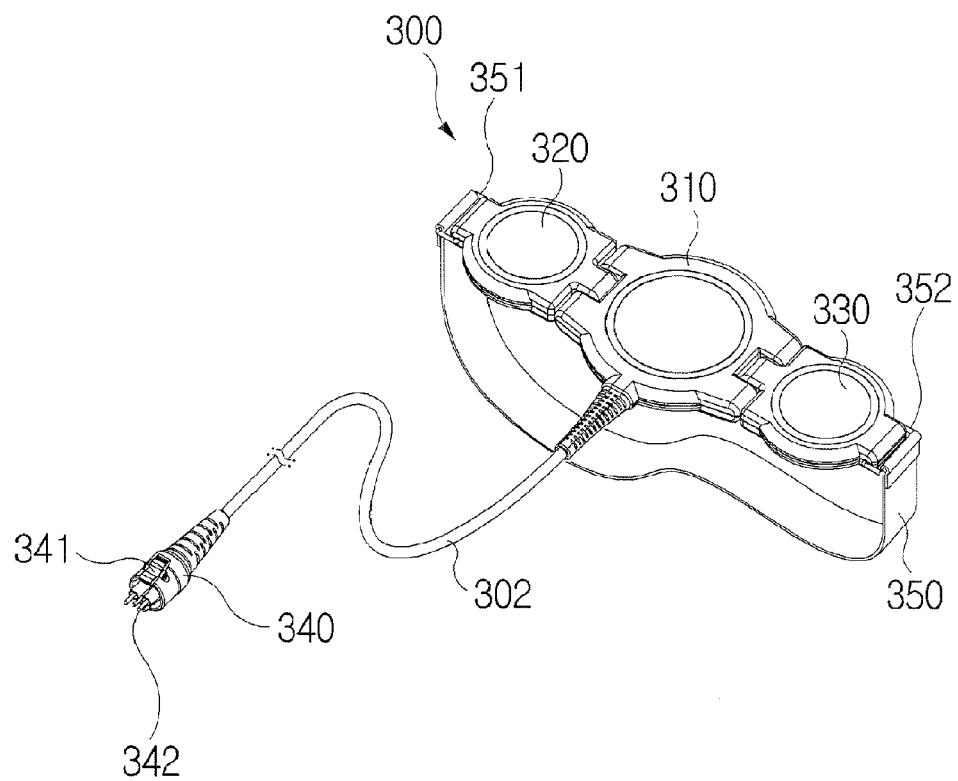
FIG. 13 is a plan perspective view illustrating a joint-type probe of the magnetic stimulation type medicalcare device according to the present invention.
Figure 14:
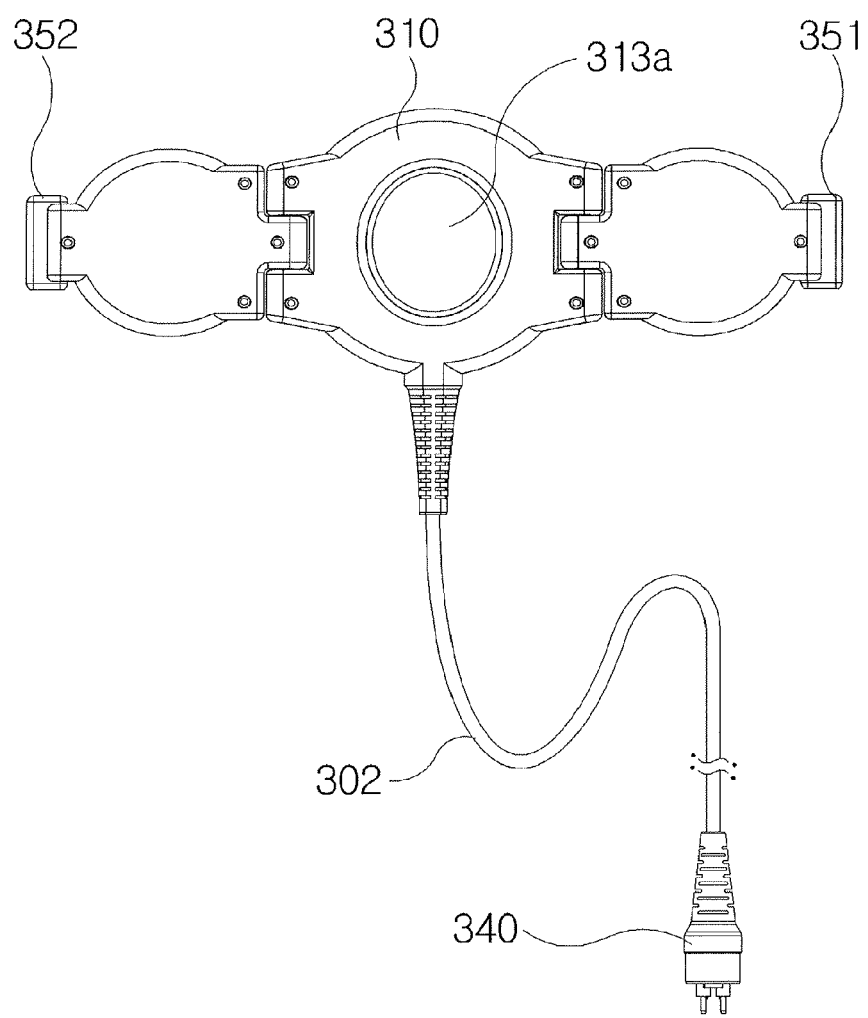
FIG. 14 is a bottom view illustrating the joint-type probe of FIG. 13.
Figure 15:
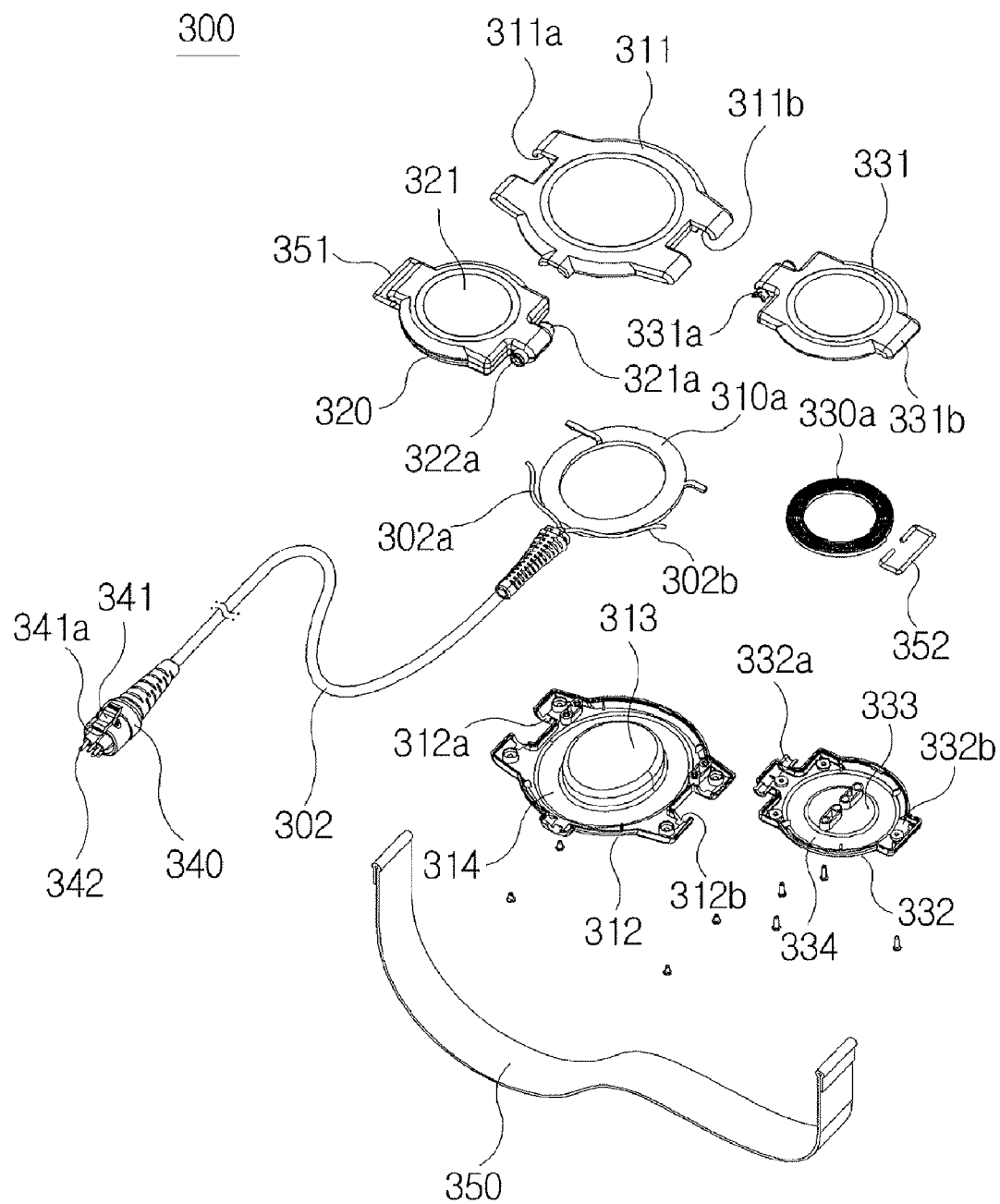
FIG. 15 is an exploded perspective view illustrating the joint-type probe of FIG. 13.
Figure 16:
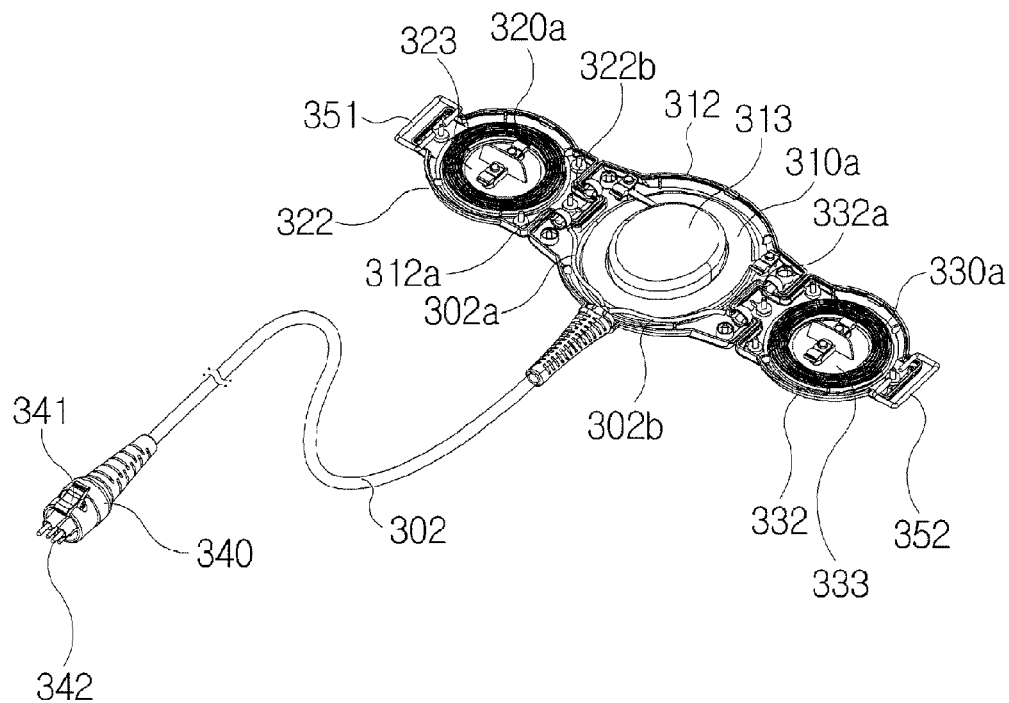
FIG. 16 is a plan perspective view illustrating an internal assembly state of the joint-type probe of FIG. 13.
Figure 17:
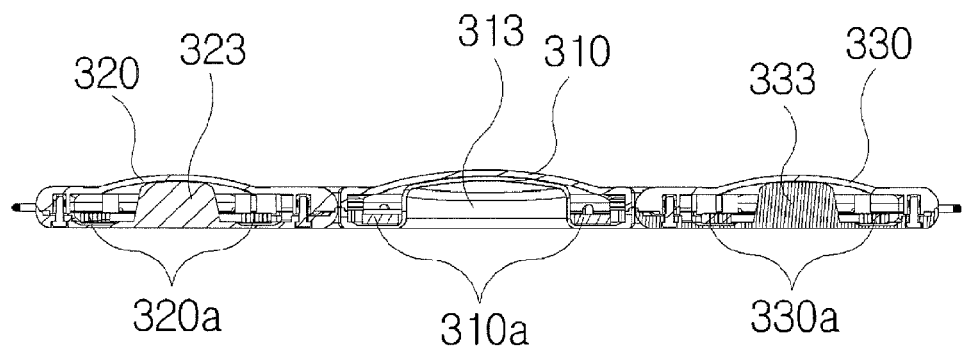
FIG. 17 is a sectional view illustrating a coupled state of the joint-type probe of FIG. 13.

FIG. 13 is a plan perspective view illustrating a joint-type probe of the magnetic stimulation type medicalcare device according to the present invention. FIG. 14 is a bottom view illustrating the joint-type probe of FIG. 13. FIG. 15 is an exploded perspective view illustrating the joint-type probe of FIG. 13. FIG. 16 is a plan perspective view illustrating an internal assembly state of the joint-type probe of FIG. 13. FIG. 17 is a sectional view illustrating a coupled state of the joint-type probe of FIG. 13.

The joint-type probe 300 may be used for a joint portion such as a knee. As shown in FIG. 1, the joint-type probe 300 may be used by connecting a connection plug 340 to the connection terminal 118 of the main body 100 of the magnetic stimulation type medicalcare device. Like the stick-type probe 200 of FIGS. 8 to 12, the connection plug 340 includes a rotatably hinged coupling member 341 and a hook protrusion 341a disposed on an end of the coupling member 341. In a state where the connection plug 340 is connected to the connection terminal 118, the connection plug 340 may be stably connected in a state where the hook protrusion 341a is hooked with the hook (see reference numeral 118a of FIG. 2) of the connection terminal 118.

In the joint-type probe 300 of the present invention, a first coil part 310a into which the discharged voltage is supplied from the main body 100 is disposed on an end of a wire part 302 extending from the connection plug 340. Also, second and third coil parts 320a and 330a into which the discharged voltage is supplied from the main body 100 are disposed on ends of lead wires 302a and 302b that are an extending part of the wire part 302, respectively.

In the current embodiment, each of the coil parts 310a, 320a, and 330a may have a hollow circular plate shape. Also, the coil parts 310a, 320a, and 330a may be received into in upper cases 311, 321, and 331 and lower cases 312, 322, and 332 for covering the coil parts 310a, 320a, and 330a.

Since the upper cases 311, 321, and 331 and lower cases 312, 322, and 332 are coupled to each other, the joint-type probe 300 may be largely classified into a first contact head 310 in which the first coil part 310a is built, a second contact head 320 in which the second coil part 320a is built, and a third contact head 330 in which the third coil part 330a is built.

Also, the joint-type probe 300 may close up by rotating the second contact head 320 and the third contact head 330 with respect to a center of the first contact head 310. For this, hinge grooves 311a, 311b, 312a, and 312b to which hinge protrusions 321a, 331a, 322a, and 332a respectively disposed on sides of the upper and lower cases 321, 331, 322, and 332 of the second and third contact heads 320, 330, 321, and 331 are coupled are defined in both ends of the upper and lower cases 311 and 312 of the first contact head 310, respectively.

Referring to the coupling structure of the first to third contact heads 310, 320, and 330 in FIGS. 15 to 17, the lower cases 312, 322, and 332 include fitting protrusions 313, 323, and 333 on centers of receiving convex parts 314, 324, and 334 on which the first to third coil parts 310a, 320a, and 330a are seated, respectively. The first to third coil parts 310a, 320a, and 330a are fixed to the fitting protrusions 313, 323, and 333 by the coupling of the upper cases 311, 321, and 331 in a state where the first and third coil parts 310a, 320a, and 330a respectively having hollow circular plate shapes are respectively fitted into the fitting protrusions 313, 323, and 333.

Also, the joint-type probe 300 of the present invention may include a fixing band 350 fixed to the joint portion such as the knee. For this, loop grooves 321b, 331b, 322b, and 332b to which loops 351 and 352 for connecting the fixing band 350 are coupled are defined in the other sides of the upper and lower cases 321, 331, 322, and 332 of the second and third contact heads 320 and 330, respectively. Here, since the upper cases 311, 321, and 331 are coupled in a state where the loops 351 and 352 are fitted, both ends of the fixing band 350 may be connected to the loops 351 and 352, respectively.

Figure 18:
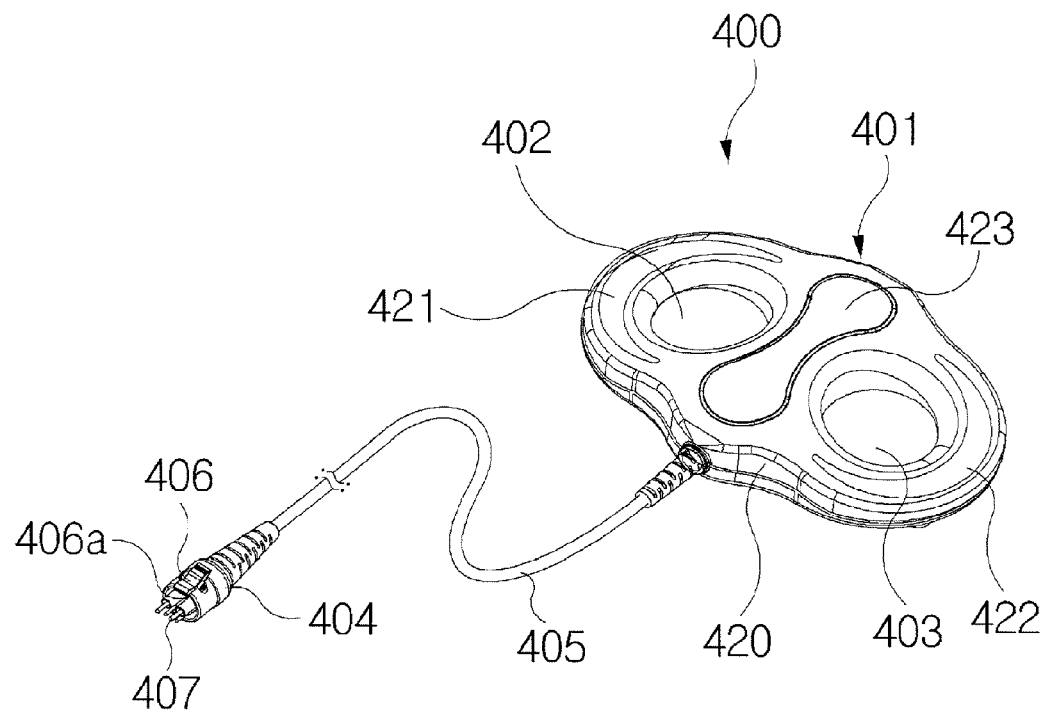
FIG. 18 is a plan perspective view illustrating a cushion-type probe of the magnetic stimulation type medicalcare device according to the present invention.
Figure 19:
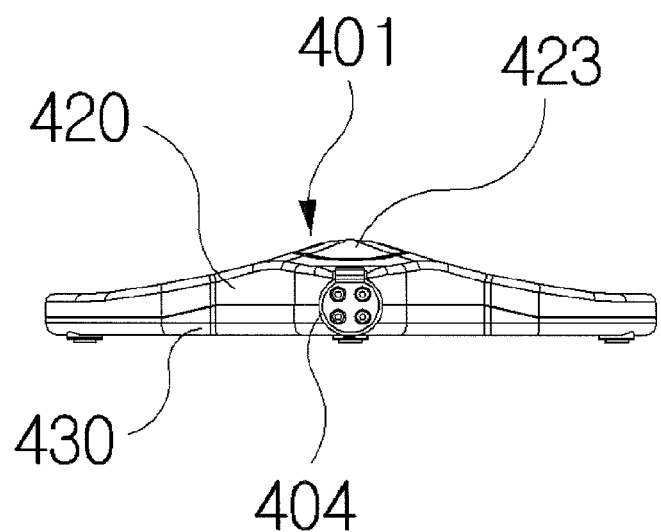
FIG. 19 is a front view illustrating the cushion-type probe of FIG. 18.
Figure 20:
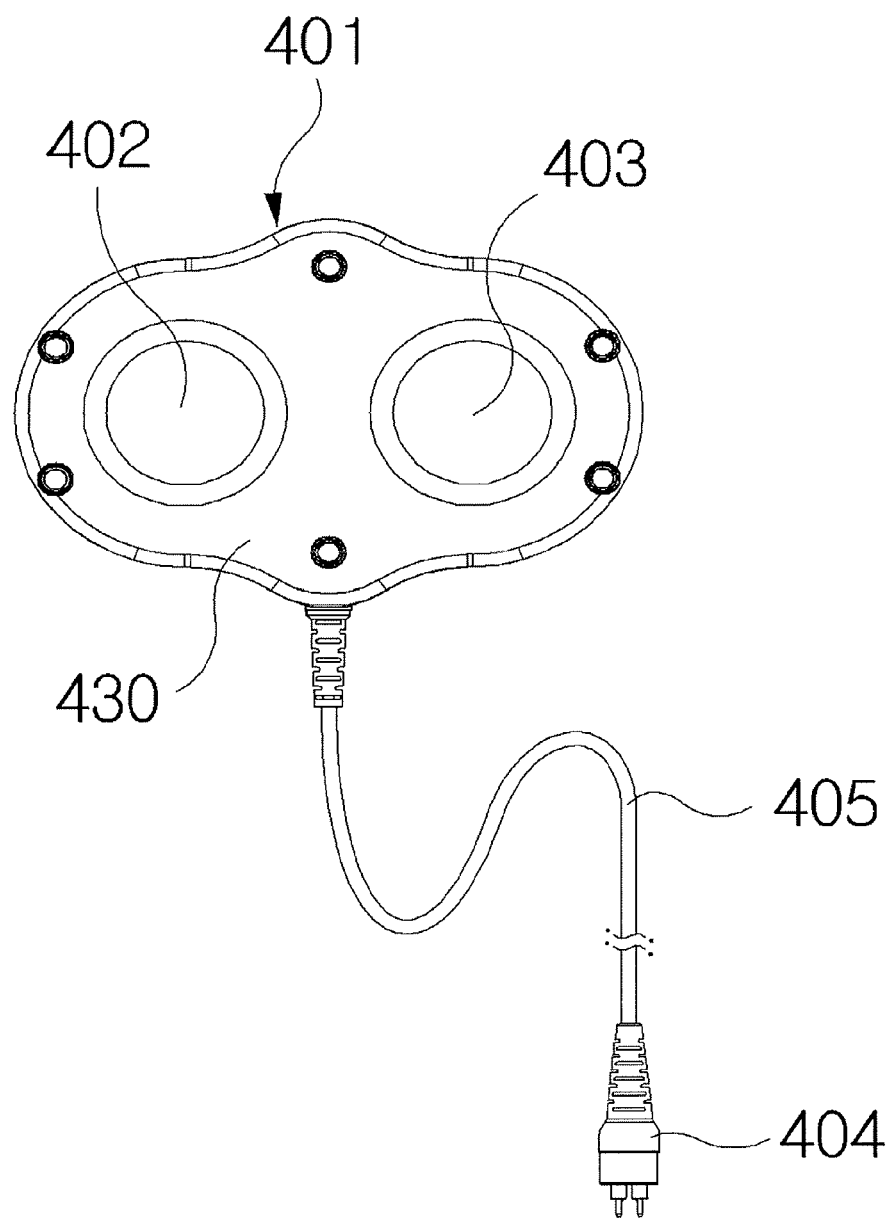
FIG. 20 is a bottom view illustrating the cushion-type probe of FIG. 18.
Figure 21:
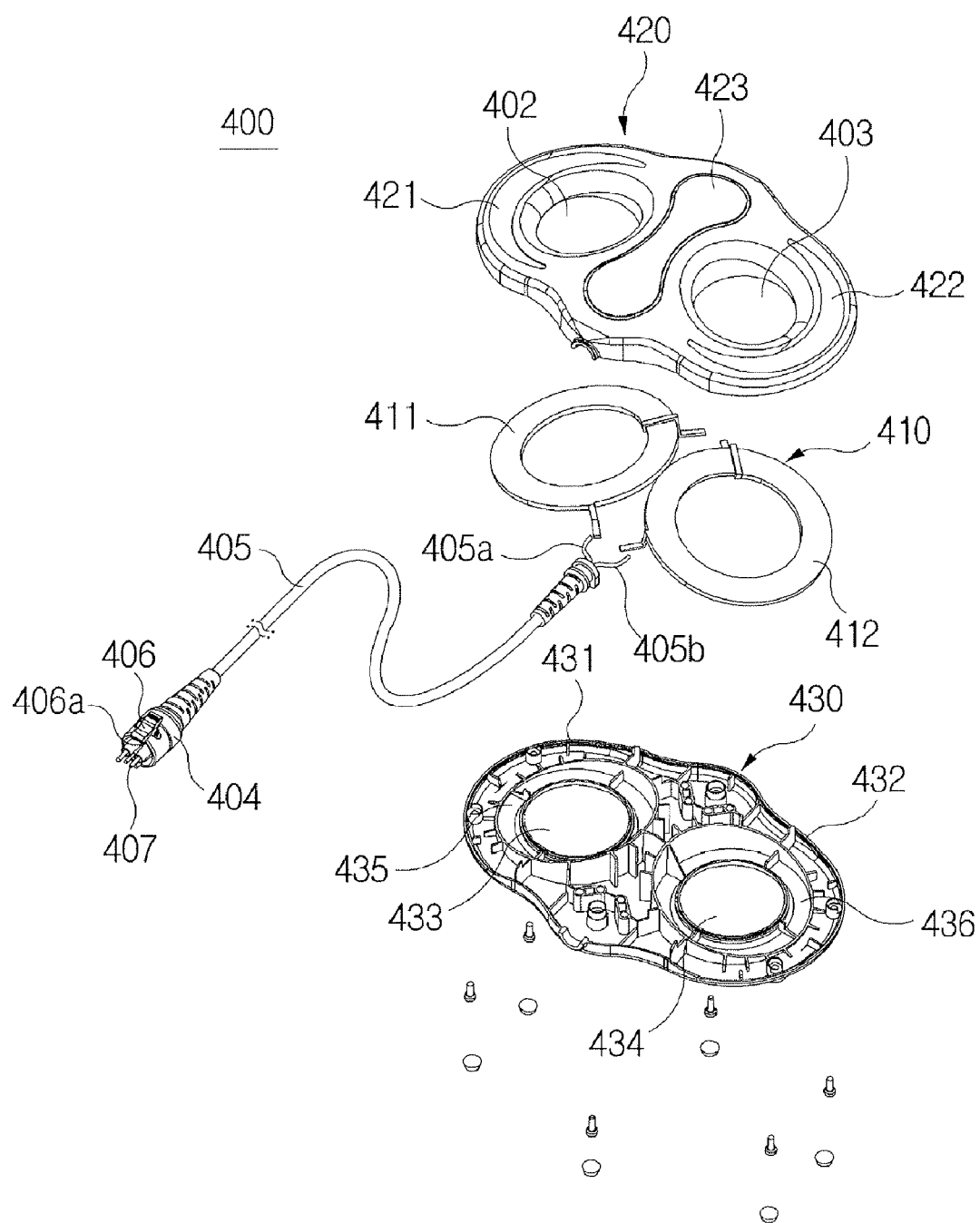
FIG. 21 is an exploded perspective view illustrating the cushion-type probe of FIG. 18.
Figure 22:
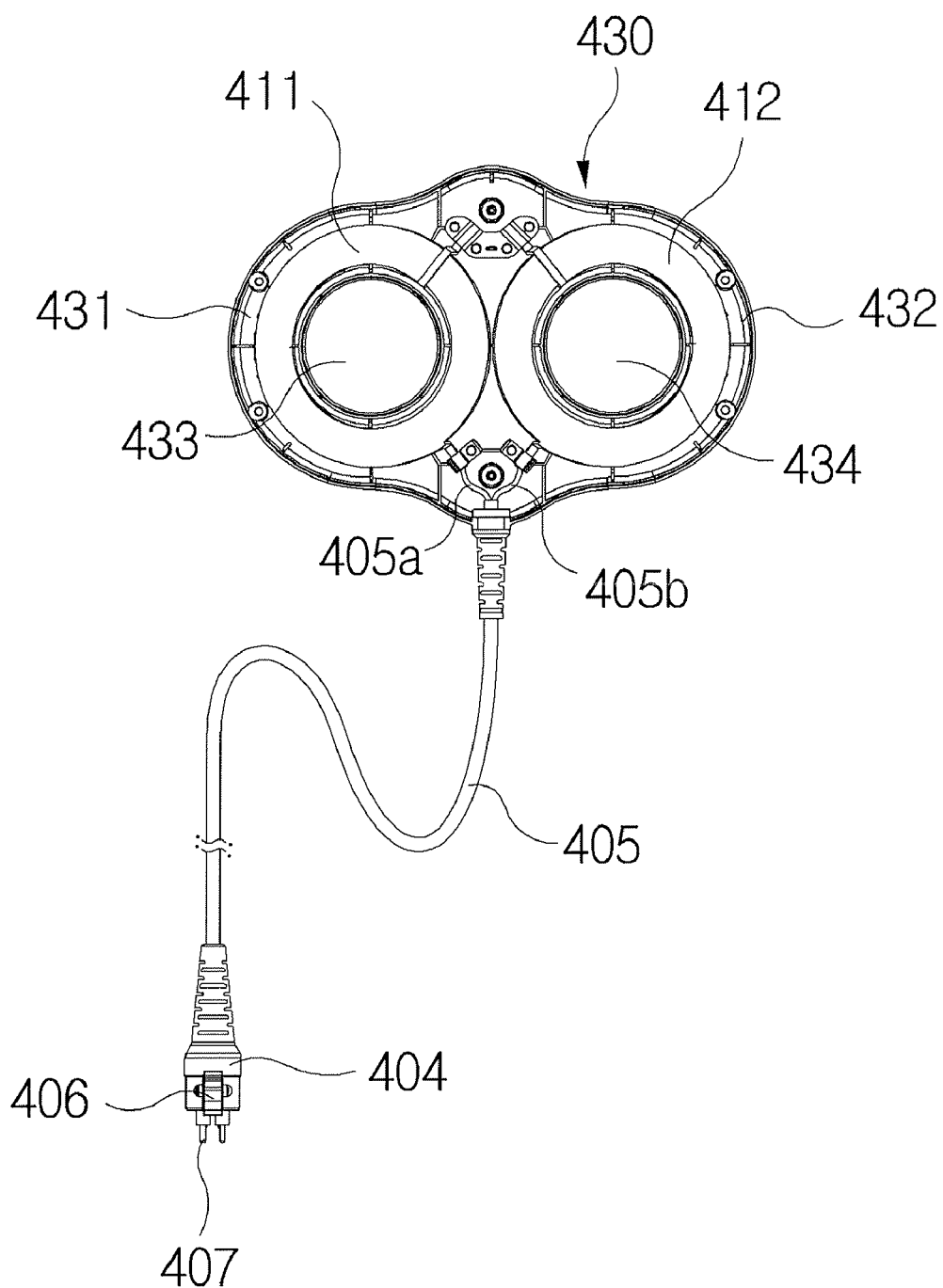
FIG. 22 is a plan view illustrating an internal assembly state of the cushion-type probe of FIG. 18.

FIG. 18 is a plan perspective view illustrating a cushion-type probe of the magnetic stimulation type medicalcare device according to the present invention. FIG. 19 is a front view illustrating the cushion-type probe of FIG. 18. FIG. 20 is a bottom view illustrating the cushion-type probe of FIG. 18. FIG. 21 is an exploded perspective view illustrating the cushion-type probe of FIG. 18. FIG. 22 is a plan view illustrating an internal assembly state of the cushion-type probe of FIG. 18.

The pelvis-type probe 400 may be used in a state where the pelvis-type probe 400 is seated on buttocks. As shown in FIG. 1, the pelvis-type probe 400 may be used by connecting a connection plug 404 to the connection terminal 118 of the main body 100 of the magnetic stimulation type medicalcare device. Like the stick-type probe 200 of FIGS. 8 to 12 and the joint-type probe 300 of FIGS. 13 to 17, the connection plug 404 includes a rotatably hinged coupling member 406 and a hook protrusion 406a disposed on an end of the coupling member 406. In a state where the connection plug 404 is connected to the connection terminal 118, the connection plug 404 may be stably connected in a state where the hook protrusion 406a is hooked with the hook (see reference numeral 118a of FIG. 2) of the connection terminal 118.

In the pelvis-type probe 400 of the present invention, a coil part into which the discharged voltage is supplied from the main body 100 is disposed on an end of a wire part 405. More particularly, a first coil part 411 and a second coil part 412 are connected to ends of lead wires 405a and 405b that is an extending part of the wire part 405, respectively.

In the current embodiment, each of the coil parts 411 and 412 may have a hollow circular plate shape. Also, the coil parts 411 and 412 may be received into in upper and lower cases 420 and 430 for covering the coil parts 411 and 412. The pelvis-type probe 400 may be classified into a first contact head 421 in which the first coil part 411 is built and a second contact head 422 in which the second coil part 412 is built.

In the upper case 420, the first and second contact heads 421 and 422 disposed on left and right sides with respect to a center of a center tip part 423 may be inclined in consideration of properties of the pelvis. Through-holes 402 and 403 passing through the first and second coil parts 411 and 412 are defined in centers of the contact heads 421 and 422, respectively.

Also, in the lower case 430, fitting protrusions 433 and 434 are disposed on centers of receiving convex parts 435 and 436 on which the first and second coil parts 411 and 412 are seated, respectively. Thus, the first and second coil parts 411 and 412 are fixed to the fitting protrusions 433 and 434 in a state where the fitting protrusions 433 and 434 are respectively fitted into the first and second coil parts 411 and 412 respectively having the hollow circular plate shapes.

As described above, the magnetic stimulation type medicalcare device of the present invention may be used through following methods.

First, as shown in FIG. 1, the connection plugs 203, 340, and 404 illustrated in FIGS. 8 to 22 are selectively connected and fixed to the connection terminal 118 of the main body 100 of the magnetic stimulation type medicalcare device.

When a power switch 132 is turned on in a state where a power source is connected to the AC voltage supply part 131 disposed on a rear surface of the main body 100, the AC voltage supplied from the AC voltage supply part 130 is boosted by the transformer 120 to charge the diode 140 and capacitor 110 while passing through the diode 140 and the capacitor 110. Then, a voltage discharge may occur in one probe 200, 300, or 400 connected to the main body 100 to perform the magnetic curing on the predetermined portion of the human body through the connected probe 200, 300, or 400.

INDUSTRIAL APPLICABILITY

As described above, the present invention relates to the magnetic stimulation type medicalcare device including the main body for generating the magnetic stimulation and the probes electrically connected to the main body to stimulate a skin of a patient through non-contact deep penetration. The magnetic stimulation type medicalcare device may be miniaturized to be used for individuals or homes. Also, the magnetic stimulation type medicalcare device may be portable and inexpensive. Since each of the probes may be detachably coupled to the main body, the probes may be easily replaced with each other according to the portions of the human body of the patient to be cured.

What is claimed is:

1. A magnetic stimulation medical care device comprising:
    a main body for generating a voltage; and
    at least one probe in which a coil for generating a magnetic field from the voltage generated in the main body is built, the at least one probe being electrically connected to the main body,
    wherein the at least one probe is electrically connected to a connection terminal of the main body by a connection plug, and the connection plug comprises a coupling member rotatably hinged where a hook protrusion is provided and is detachably connected to the connection terminal and where the hook protrusion is hooked with a hook disposed on an end of the connection terminal.

2. The magnetic stimulation medical care device according to claim 1, wherein the main body comprises the following components:
    an alternating current (AC) voltage supply part;
    a transformer connected to the AC voltage supply part to boost an AC voltage;
    a voltage supply regulation part for regulating the AC voltage flowing from the AC voltage supply part into the transformer;
    a diode for rectifying and charging the AC voltage boosted by the transformer; and
    a control part for discharging the voltage into the coil within the probe and controlling the AC voltage regulation by the AC supply regulation part.

3. The magnetic stimulation medical care device according to claim 1, wherein the main body comprises a handle for portable use, front and rear covers, and left and right covers for covering left and right opened sides thereof,
    wherein the front and rear covers and the left and right covers are assembled or dissembled with each other, and a plurality of support legs corresponding to each other protrude from lower ends of the front and rear covers so that the front and rear covers stand upright.

4. The magnetic stimulation medical care device according to claim 2, wherein the main body further comprises the following components: an LCD module that is a display unit, a button assembly on which a plurality of manipulation buttons are assembled, and a connection terminal for connecting the at least one probe to each other, and the control part controls an overall operation of the device with respect to operations of the components of said device due to the manipulation of the manipulation buttons.

5. The magnetic stimulation medical care device according to claim 3, wherein the main body further comprises an upper cover having a circular shape on an upper central portion thereof, each of the front and rear covers comprises a semicircular-shaped uneven part on an upper central portion thereof, and the upper cover is fixed by hooks coupling the front cover and the rear cover.

6. The magnetic stimulation medical care device according to claim 5, wherein hook protrusions connected to an upper portion of the main body protrude from both ends of the handle in left and right directions,
    hook grooves to which the hook protrusions are fixed by hooks after a coupling of the front and rear covers are defined outside the semicircular-shaped uneven parts of the front and rear covers, respectively.

7. The magnetic stimulation medical care device according to claim 1, wherein the at least one probe comprises a wire part that is an extending part of a lead wire and a coil part into which a discharged voltage is supplied from the main body at an end of the wire part, and the wire part and the coil part are divided into a stick part in which the wire part is built and a head part in which the coil part is built in the wire part and the coil part is received into upper and lower case members for covering the wire part and the coil part.

8. The magnetic stimulation medical care device according to claim 7, wherein the lower case member comprises a fitting protrusion at a center of a receiving convex part on which the coil part is seated, and the coil part is fixed by a coupling of the upper case member in a state where the coil part is fitted into the fitting protrusion.

9. The magnetic stimulation medical care device according to claim 8, wherein the upper case member and the lower case member comprise a body case for receiving the wire part and a head case for receiving the coil part, a hinge member is connected between the body case and the head case, and the head part is rotatable with respect to a center of the hinge member according to an angle of a portion of a human body for using the at least one probe.

10. The magnetic stimulation medical care device according to claim 7, wherein the coil part has a hollow circular plate shape.

\* \* \* \* \*